United States Patent
Foschini et al.

(10) Patent No.: US 12,027,277 B1
(45) Date of Patent: Jul. 2, 2024

(54) ACTIVE LEARNING FOR WEARABLE HEALTH SENSOR

(71) Applicant: Evidation Health, Inc., San Mateo, CA (US)

(72) Inventors: Luca Foschini, Santa Barbara, CA (US); Andrea Varsavsky, Santa Monica, CA (US); Raghunandan Melkote Kainkaryam, Cincinnati, OH (US)

(73) Assignee: Evidation Health, Inc., San Mateo, CA (US)

( * ) Notice: Subject to any disclaimer, the term of this patent is extended or adjusted under 35 U.S.C. 154(b) by 421 days.

(21) Appl. No.: 17/111,765

(22) Filed: Dec. 4, 2020

Related U.S. Application Data

(60) Provisional application No. 62/944,286, filed on Dec. 5, 2019.

(51) Int. Cl.
  *G16H 50/70* (2018.01)
  *A61B 5/00* (2006.01)
  (Continued)

(52) U.S. Cl.
  CPC ........... *G16H 50/70* (2018.01); *A61B 5/7267* (2013.01); *G06N 5/04* (2013.01); *G06N 20/00* (2019.01);
  (Continued)

(58) Field of Classification Search
  CPC ......... G16H 10/00–80/00; G06N 3/00–99/007
  See application file for complete search history.

(56) References Cited

U.S. PATENT DOCUMENTS

| | | |
|---|---|---|
| 7,937,461 B2 | 5/2011 | Kutzik et al. |
| 10,327,697 B1 | 6/2019 | Stein et al. |

(Continued)

FOREIGN PATENT DOCUMENTS

| | | |
|---|---|---|
| IN | 202041010784 | 11/2020 |
| WO | WO-2014039881 A1 | 3/2014 |

(Continued)

OTHER PUBLICATIONS

Avati et al., "Improving palliative care with deep learning," Avati et al. BMC Medical Informatics and DecisionMaking 2018, 18(Suppl 4):122; https://doi.org/10.1186/s12911-018-0677-8. (Year: 2018).*

(Continued)

*Primary Examiner* — Jonathon A. Szumny
(74) *Attorney, Agent, or Firm* — Wilson Sonsini Goodrich & Rosati

(57) ABSTRACT

An active learning system can analyze a dataset of users with self-reported symptoms and associated data from wearable devices to train a baseline machine learning model to predict symptoms of a chronic health condition based on wearable device data. For example, symptoms can be predicted in terms of lost physical activity, increased sleep requirements, and changes in resting heart rate. Using the baseline model, the active learning system can train and refine individual user-specific models to predict the onset of chronic health condition symptoms over time. These models can be used to predict symptoms for inclusion in a log of symptoms for the target user (which may be used by a healthcare provider to personalize treatment for the target user) or to provide interventions to the user (for example, warning of a predicted severe symptom day). In some implementations individual chronic health condition models are maintained and updated using active learning techniques.

19 Claims, 6 Drawing Sheets

(51) Int. Cl.
| | |
|---|---|
| *G06N 5/04* | (2023.01) |
| *G06N 20/00* | (2019.01) |
| *G16H 10/60* | (2018.01) |
| *G16H 40/67* | (2018.01) |
| *G16H 50/20* | (2018.01) |
| *G16H 50/30* | (2018.01) |
| *G16H 50/50* | (2018.01) |
| *A61B 5/024* | (2006.01) |
| *A61B 5/0533* | (2021.01) |
| *A61B 5/08* | (2006.01) |
| *A61B 5/11* | (2006.01) |

(52) U.S. Cl.
CPC ............ *G16H 10/60* (2018.01); *G16H 40/67* (2018.01); *G16H 50/20* (2018.01); *G16H 50/30* (2018.01); *G16H 50/50* (2018.01); *A61B 5/02405* (2013.01); *A61B 5/02438* (2013.01); *A61B 5/0533* (2013.01); *A61B 5/0816* (2013.01); *A61B 5/1118* (2013.01); *A61B 5/4806* (2013.01)

(56) References Cited

U.S. PATENT DOCUMENTS

| | | | |
|---|---|---|---|
| 10,524,697 | B2 | 1/2020 | Gubbi Lakshminarasimha et al. |
| 11,387,000 | B2 | 7/2022 | Saliman et al. |
| 11,471,115 | B2 | 10/2022 | Rance et al. |
| 2005/0228691 | A1 | 10/2005 | Paparo |
| 2008/0146334 | A1 | 6/2008 | Kil |
| 2008/0214903 | A1 | 9/2008 | Orbach |
| 2008/0319786 | A1 | 12/2008 | Stivoric et al. |
| 2009/0006457 | A1 | 1/2009 | Stivoric et al. |
| 2011/0184250 | A1 | 7/2011 | Schmidt et al. |
| 2012/0046966 | A1 | 2/2012 | Chang et al. |
| 2012/0246102 | A1 | 9/2012 | Sudharsan |
| 2014/0005502 | A1* | 1/2014 | Klap ............... A61B 5/1116 600/300 |
| 2014/0129247 | A1 | 5/2014 | Op Den Buijs et al. |
| 2014/0188512 | A1* | 7/2014 | Parker ............... G16H 10/60 705/3 |
| 2014/0278449 | A1* | 9/2014 | Kharraz Tavakol ... G06Q 10/10 705/2 |
| 2014/0315168 | A1* | 10/2014 | Movellan ............. G16H 20/70 434/236 |
| 2015/0006456 | A1 | 1/2015 | Sudharsan |
| 2015/0242518 | A1* | 8/2015 | Rosenbaum ......... G06F 16/285 707/754 |
| 2016/0089089 | A1 | 3/2016 | Kakkar et al. |
| 2016/0328991 | A1* | 11/2016 | Simpson ............ G09B 19/0092 |
| 2016/0361020 | A1 | 12/2016 | LeBoeuf et al. |
| 2017/0140109 | A1* | 5/2017 | Kheifetz ............... G16H 50/50 |
| 2017/0188841 | A1* | 7/2017 | Ma ..................... A61B 5/0008 |
| 2017/0206795 | A1 | 7/2017 | Kaleal, III |
| 2017/0245808 | A1 | 8/2017 | Jain et al. |
| 2017/0293846 | A1* | 10/2017 | Zyglowicz ............... A61B 5/20 |
| 2018/0330824 | A1* | 11/2018 | Athey ..................... G16B 40/20 |
| 2018/0338733 | A1 | 11/2018 | Jain et al. |
| 2018/0344215 | A1 | 12/2018 | Ohnemus et al. |
| 2018/0350451 | A1* | 12/2018 | Ohnemus ............. H04L 67/535 |
| 2019/0066845 | A1* | 2/2019 | Roy ..................... G16H 15/00 |
| 2019/0076031 | A1* | 3/2019 | Valys ................. A61B 5/02405 |
| 2019/0209022 | A1 | 7/2019 | Sobol et al. |
| 2019/0245824 | A1* | 8/2019 | Hiir ..................... G06Q 10/107 |
| 2019/0355472 | A1 | 11/2019 | Kutzko |
| 2019/0385711 | A1* | 12/2019 | Shriberg ............... G16H 50/20 |
| 2020/0135334 | A1* | 4/2020 | Rajasekhar ............ G10L 15/26 |
| 2020/0161005 | A1* | 5/2020 | Lyman ............. G06F 18/24155 |
| 2020/0273578 | A1 | 8/2020 | Kutzko et al. |
| 2021/0038163 | A1* | 2/2021 | Agrawal ............... A61B 5/4839 |
| 2021/0042667 | A1* | 2/2021 | Ghosh ..................... G06N 20/20 |
| 2021/0117417 | A1 | 4/2021 | Hendrickson et al. |
| 2021/0151194 | A1 | 5/2021 | Foschini et al. |
| 2021/0158214 | A1 | 5/2021 | Witt et al. |
| 2021/0166803 | A1* | 6/2021 | Ellis ..................... G06V 10/776 |
| 2021/0174919 | A1 | 6/2021 | Vaughan |
| 2021/0204914 | A1* | 7/2021 | Meral .................. A61B 5/0035 |
| 2021/0241923 | A1 | 8/2021 | Foschini et al. |
| 2021/0319887 | A1 | 10/2021 | Derrick, Jr. et al. |

FOREIGN PATENT DOCUMENTS

| | | |
|---|---|---|
| WO | WO-2019165004 A1 | 8/2019 |
| WO | WO-2021127566 A1 | 6/2021 |
| WO | WO-2021154401 A1 | 8/2021 |
| WO | WO-2022200985 A1 | 9/2022 |

OTHER PUBLICATIONS

Enshaeifar et al., "Machine learning methods for detecting urinary tract infection and analysing daily living activities in people with dementia," PLoS ONE 14(1): e0209909; https://doi.org/10.1371/journal.pone.0209909. (Year: 2019).*
Amin et al., "Personalized Health Monitoring using Predictive Analytics," 2019 IEEE Fifth International Conference on Big Data Computing Service and Applications (BigDataService); DOI 10.1109/BigDataService.2019.00048. (Year: 2019).*
PCT/US2022/043874 International Search Report and Written Opinion dated Nov. 17, 2022.
U.S. Appl. No. 17/946,975 Non-Final Office Acton dated Nov. 17, 2022.
Co-pending U.S. Appl. No. 17/946,975, inventors Clay; Ieuan et al., filed Sep. 16, 2022.
Co-pending U.S. Appl. No. 18/148,991, inventors Foschini; Luca et al., filed Dec. 30, 2022.
Co-pending U.S. Appl. No. 18/156,010, inventors Foschini; Luca et al., filed Jan. 18, 2023.
Homayounfar et al.: Data mining research trends in computerized patient records. 2011 Federated Conference on Computer Science and Information Systems (FedCSIS), pp. 133-139 (2011).
Mezlini et al.: Estimating the Burden of Influenza-like Illness on Daily Activity at the Population Scale Using Commercial Wearable Sensors. JAMA Netw Open. 5(5):e2211958:1-12 doi:10.1001/jamanetworkopen.2022.11958 (2022).
Pavel et al.: Behavioral Informatics and Computational Modeling in Support of Proactive Health Management and Care. IEEE Transactions on Biomedical Engineering. 62(12):2763-2775 doi:10.1109/TBME.2015.2484286 (2015).
Pentland: Healthwear: medical technology becomes wearable. Computer 37(5), pp. 42-49 doi:10.1109/MC.2004.1297238 (2004).
U.S. Appl. No. 16/926,510 Final Office Action dated Jan. 19, 2023.
U.S. Appl. No. 16/953,256 Non-Final Office Action dated Jan. 5, 2023.
U.S. Appl. No. 17/946,975 Non-Final Office Action restarting Office Action dated Nov. 17, 2022, dated Jan. 11, 2023.
U.S. Appl. No. 17/968,413 Non-Final Office Action dated Jan. 3, 2023.
Co-pending U.S. Appl. No. 17/968,413, inventors Foschini; Luca et al., filed Oct. 18, 2022.
Althouse et al.: Enhancing disease surveillance with novel data streams: challenges and opportunities. EPJ Data Sci. 4(1):17, pp. 1-8 doi:10.1140/epjds/s13688-015-0054-0 (2015).
Evidation Health: Achievement. Publication Date Unknown, six pages, [Retrieved online Nov. 4, 2020] URL: https://www.myachievement.com/.
Henning: What is Syndromic Surveillance ?. MMWR Suppl. 53:5-11 (2004).
Li et al.: Digital Health: Tracking Physiomes and Activity Using Wearable Biosensors Reveals Useful Health-Related Information. PLoS Biology, pp. 1-30 DOI:10.1371/journal.pbio.2001402(2017).
PCT/US2020/064369 International Search Report and Written Opinion dated Mar. 2, 2021.
Radin et al.: Harnessing wearable device data to improve state-level real-time surveillance of influenza-like illness in the USA: a population-based study. Lancet Digit Health 2(2):e85-e93 doi:10.1016/S2589-7500(19)30222-5 (2020).

(56) References Cited

OTHER PUBLICATIONS

Simonsen et al.: Infectious Disease Surveillance in the Big Data Era: Towards Faster and Locally Relevant Systems. J Infect Dis. 214(suppl_4):S380-S385 doi:10.1093/infdis/jiw376 (2016).
U.S. Appl. No. 14/977,194 Final Office Action dated Dec. 16, 2016.
U.S. Appl. No. 14/977,194 Final Office Action dated Jul. 12, 2018.
U.S. Appl. No. 14/977,194 Final Office Action dated May 21, 2020.
U.S. Appl. No. 14/977,194 Non-Final Office Action dated Aug. 30, 2017.
U.S. Appl. No. 14/977,194 Non-Final Office Action dated Feb. 25, 2016.
U.S. Appl. No. 14/977,194 Non-Final Office Action dated Sep. 26, 2019.
U.S. Appl. No. 16/926,510 Non-Final Office Action dated Jul. 8, 2022.
U.S. Food & Drug Administration: Real-World Evidence, pp. 1-3 [Retrieved online Nov. 4, 2020] URL: https://www.fda.goviscience-research/science-and-research-special-topics/real-world-evidence (published Mar. 23, 2020).
Wang et al.: Unsupervised learning of disease progression models. KDD '14: Proceedings of the 20th ACM SIGKDD international conference on Knowledge discovery and data mining, pp. 85-94 URL:https://doi.org/10.1145/2623330.2623754 (Aug. 2014).
Cao, B. et al., "DeepMood: Modeling Mobile Phone Typing Dynamics for Mood Detection," arXiv:1803.08986, Mar. 23, 2018, pp. 1-9.
Daly, R.M. et al., "Risk stratification and daily symptom monitoring for oncology patients," Journal of Clinical Oncology, vol. 37, Iss. 15, Suppl. 6535, May 20, 2019, pp. 6535.
Element AI, "Element AI makes its BAyesian Active Learning library open source," Oct. 8, 2019, six pages, [Online] [Retrieved on Jan. 21, 2021] Retrieved from the Internet <URL: https://www.elementai.com/news/2019/element-ai-makes-its-bayesian-active-learning-library-open-source>.
Gal, Y. et al., "Bayesian convolutional neural networks with Bernoulli approximate variational inference," ICLR workshop track, arXiv:1506.02158, Jan. 18, 2016, pp. 1-12.
Gal, Y. et al., "Deep Bayesian Active Learning with Image Data," arXiv: 1703.02910, Mar. 8, 2017, pp. 1-10.
Gal, Y. et al., "Dropout as a Bayesian approximation: Representing model uncertainty in deep learning," International Conference on Machine Learning, Jun. 2016, pp. 1-10.
Hochreiter, S. et al., "Long short-term memory," Neural Computation 9(8), 1997, pp. 1-32.
Houlsby, N. et al., "Bayesian Active Learning for Classification and Preference Learning," arXiv:1112.5745, Dec. 24, 2011, pp. 1-17.
Nelson, S.H et al., "Continuous, objective measurement of physical activity during chemotherapy for breast cancer: the Activity in Treatment pilot study," Translational Behavioral Medicine, vol. 10, No. 4, May 29, 2020, pp. 1031-1038.
Schroeder, J. et al., "Examining Self-Tracking by People with Migraine: Goals, Needs, and Opportunities in a Chronic Health Condition," DIS '18, Jun. 2018, pp. 135-148.
Turner, J., "New directions in communications (or which way to the information age?)," IEEE Communications Magazine 24(10), Oct. 1986, pp. 8-15.

* cited by examiner

ACTIVE LEARNING FOR WEARABLE HEALTH SENSOR

CROSS REFERENCE TO RELATED APPLICATIONS

This application claims priority to U.S. Provisional Application No. 62/944,286, filed Dec. 5, 2019, which is hereby incorporated by reference.

BACKGROUND

This disclosure generally relates to managing and, in particular, to predicting, detecting, and mitigating the effects of a chronic health condition based on sensor data.

Chronic health conditions can cause long-term symptoms which can manifest unpredictably over time in affected individuals. For example, an individual can experience high day-to-day variability in symptoms of a chronic health condition based on characteristics or causes dependent on that individual. Healthcare providers can personalize treatment plans for an individual affected by a chronic health condition to account for that individual's unique condition (for example, controlling the dosing or composition of a medication). However, effective personalization of treatment plans can rely on an accurate record of the individual's symptoms stemming from the chronic health condition, which (for most chronic health conditions) is left up to the affected individual to self-track and log chronic health condition symptoms each day over a long period of time. While self-tracking may be effective in the short term, over time individuals may grow tired of logging chronic health condition symptoms and may stop self-tracking or resort to less accurate methods (such as attempting to recall and record symptoms for an entire month at one time, which can result in an incomplete recollection of symptoms). However, use of an inaccurate or incomplete log of chronic health condition symptoms can compromise the ability of a healthcare provider to effectively personalize a treatment plan for that individual.

SUMMARY

Sensor data about a user (for example, from wearable devices) can reflect physiological and behavioral changes associated with chronic disease symptoms (for example, the severity of chronic pain or the likelihood of getting a migraine headache in an individual) or other chronic health conditions.

An active learning system can analyze a dataset of users with self-reported symptoms and associated data from wearable devices to determine a baseline model to predict symptoms of a chronic health condition based on wearable device data. For example, symptoms can be predicted in terms of lost physical activity, increased sleep requirements, and changes in resting heart rate. Using a baseline model, the active learning system can deploy and refine individual user-specific models to predict chronic health condition symptoms. These models can be used to predict symptoms for inclusion in a log of symptoms for the target user (which may be used by a healthcare provider to personalize treatment for the target user) or to provide interventions to the user (for example, warning of a predicted severe symptom day). In some implementations individual chronic health condition models are maintained and updated using active learning techniques.

Figure 1:
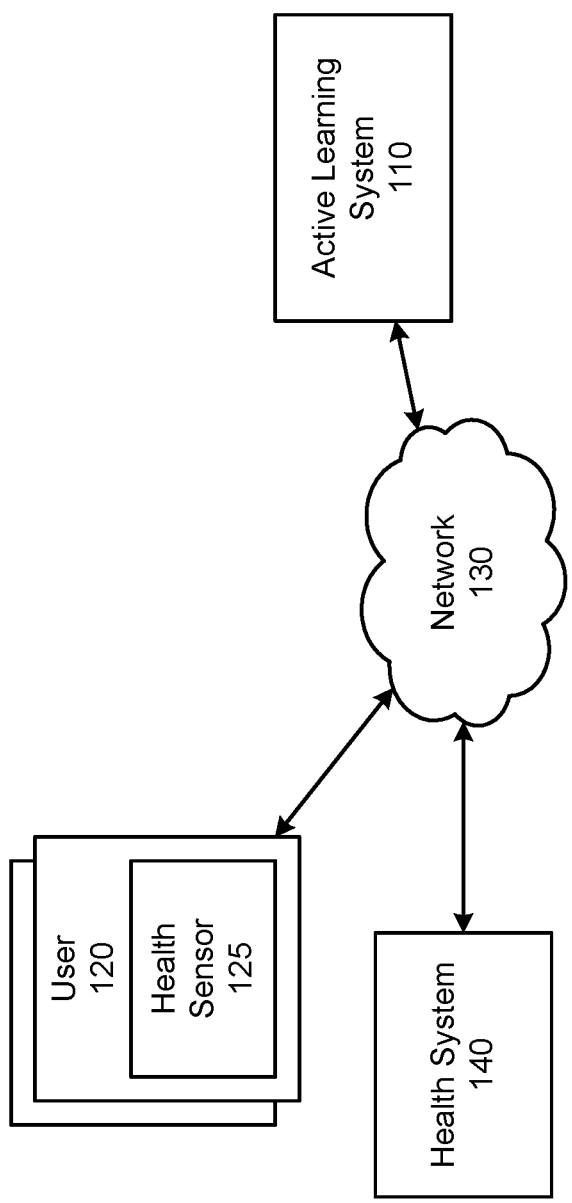
FIG. 1 is a block diagram of a system environment in which an active learning system operates, in accordance with an embodiment.

The figures depict various embodiments for purposes of illustration only. One skilled in the art will readily recognize from the following discussion that alternative embodiments of the structures and methods illustrated herein may be employed without departing from the principles described herein. The figures use like reference numerals to identify like elements. A letter after a reference numeral, such as "110A," indicates the text refers specifically to the element having that particular reference numeral. A reference numeral in the text without a following letter, such as "102," refers to any or all of the elements in the figures bearing that reference numeral (e.g., "110" in the text refers to reference numerals "110A" and "110B" in the figures).

DESCRIPTION

An active learning system can utilize sensor data reflecting physiological and behavioral changes associated with symptoms of a chronic health condition to predict the future symptoms of the chronic health condition for an individual with the chronic health condition. A chronic health condition (herein, a CHC) is, as used herein, an illness, disease, injury, or other health state associated with physiological and/or behavioral symptoms (herein, CHC symptoms) over an extended period. For example, a chronic health condition can be chronic pain, migraine headaches, multiple sclerosis, cancer, COPD (Chronic Obstructive Pulmonary Disease), a physical injury, or a treatment regimen with side effects that must be managed, such as chemotherapy. CHC symptoms can display high day-to-day variability in severity (for example, chronic pain that is noticeably worse on certain days) or may flare up erratically (such as with infrequently occurring migraine headaches).

In some embodiments, an active learning system can predict daily CHC symptom severity for an individual using an individualized model of the CHC for that individual. Implementations of an active learning system can use active learning (a branch of machine learning) techniques to request input from the individual as needed to confirm (or refute) predictions by the active learning system. The individual's feedback can then be used to improve future predications by the active learning system for that individual. For example, an active learning system can assemble daily CHC symptom predictions made by the active learning system or self-reported CHC symptoms received from the individual into a log of CHC symptoms that can later be used by a healthcare provider (or other entity) to create or modify an individual treatment plan, aid in determining triggering conditions affecting CHC symptom severity, or otherwise manage the individual's CHC.

System Overview

FIG. 1 is a block diagram of a system environment in which an active learning system operates, in accordance with an embodiment. The environment 100 of FIG. 1 includes an active learning system 110, a set of users 120, each associated with one or more health sensors 125, a network 130, and a health system 140.

The active learning system 110 is a server, server cluster, or cloud-based server capable of predicting CHC symptoms for a user 120 within a population based on physical statistics received from that user 120. In some embodiments, the active learning system 110 gathers physical statistics about a set of users 120 within a population (for example, through data from one or more health sensors monitoring the physical statistics of users 120) and uses the resulting data to predict CHC symptoms for those users 120. As used herein, physical statistics are measurements characterizing a user's activity level or current health state (such as from health sensors 125 or other sources as will be discussed below). For example, physical statistics can include measurements of the user's vital signs such as resting heart rate (RHR), current heart rate (for example, presented as a time series), heart rate variability, respiration rate, or galvanic skin response, measurements of user activity such as daily number of steps, distance walked, time active, or exercise amount, sleep statistics such as time slept, number of times sleep was interrupted, or sleep start and end times, and/or other similar metrics. As used herein, physical statistic data includes measures of one or more physical statistics of a user. The active learning system 110 can analyze received physical statistic data measuring user physical statistics to extrapolate a baseline (population level) CHC model for the population of users 120. Similarly, the active learning system can generate individual CHC models to predict CHC symptoms for individual users 120 within the population. In some embodiments described herein, CHC symptom predictions are made on a daily basis, however an individual CHC model can also make predictions for other time periods in other embodiments (for example, hourly predictions, weekly predictions, or the like). In some implementations, the active learning system 110 can request a user 120 to provide feedback (including a CHC symptom report and/or confirmation of a predicted CHC symptom) to improve the individual model for that user 120. The active learning system 110 can perform or recommend interventions to user 120 or associated health system 140 or generate a log of CHC symptom predictions over time (which may later be sent to the user 120 or the health system 140). The active learning system 110 will be discussed further below.

As used herein, an "intervention" is an action initiated by the active learning system 110 to reduce, mitigate, or otherwise respond to predicted CHC symptoms for a user 120. In some implementations, one or more interventions are directly performed by the active learning system 110, such as providing a recommendation to the user 120 (for example, via a user device), however other interventions may require additional resources or authorization not available to the active learning system 110. As will be discussed below, interventions recommended by the active learning system 110 can depend on the CHC and the specific predictions made by the active learning system 110. For example, in some implementations an active learning system 110 can predict that an individual user 120 will experience severe CHC symptoms today and recommend behavior modifications or additional treatment of the CHC to mitigate the impact of the predicted severe CHC symptoms.

Each user 120 of the active learning system 110 is a member of a population monitored by the active learning system 110 for one or more CHCs. A user 120 can interact with health sensors 125 and the active learning system 110 through a user device such as a mobile device, laptop or desktop computer, or other similar computing device. For example, a user 120 can be asked to provide feedback on one or more CHC symptoms predicted by the active learning system 110 and may do so through an associated user device. In some implementations, each user 120 is a member of one or more population cohorts characterized by demographic information, geographic location, user characteristics and/or other similar factors which may affect the manifestation of the CHC in that user 120.

In some embodiments, each user 120 is associated with a set of health sensors 125 measuring physical statistics of that user 120. For example, the set of health sensors 125 associated with a user 120 can measure the user's resting heart rate (RHR) over time, a daily number of steps (and/or other measure of activity level such as distance walked), and sleep statistics (such as time slept, number of times sleep was interrupted, sleep start and end times, etc.) for the user 120. Recorded physical statistics from health sensors 125 can be stored as physical statistic data and sent by the health sensor 125 to the active learning system 110 for analysis. In some implementations, some or all physical statistic data is collected in the form of time series data periodically recording measurements of physical statistics of the user 120 over time. The frequency of measurements included in the physical statistics data sent to the active learning system 110 can depend on the health sensor 125, user preference selections, and the type of physical statistic data being collected. For example, a health sensor 125 may send time series data for average RHR multiple times per day, but only send hours slept data once per day. In some implementations, the health sensor 125 sends physical statistic data to the active learning system 110 frequently, for example hourly or in real time. A health sensor 125 can be a wearable device or other device capable of providing physical statistics about the user 120. For example, a health sensor 125 can be a dedicated fitness tracker, a pedometer, a sleep tracker, a smart watch, smartphone, or mobile device with physical statistic monitoring functionality. For example, a health sensor 125 can be a smartphone of the user 120 with an installed physical statistic monitoring application using one or more sensors of the smartphone to measure steps, activity, movement, sleep time, or other physical statistics. An individual user 120 can be associated with multiple health sensors 125 measuring overlapping or distinct physical statistics about the user 120. The physical statistic data gathered by health sensors 125 can be sent to the active learning system 110 directly from the health sensor 125, manually uploaded to the active learning system 110 by the associated user 120 or transmitted via a third-party system to the active learning system 110. For example, the user 120 may authorize a third-party service associated with a health sensor 125 to transmit physical activity data to the active learning system 110. A user 120 or a health sensor 125 associated with a user 120 can communicate with the active learning system 110 over the network 130.

The network 130 is a network or system of networks connecting the active learning system 110 to the set of users 120 and/or health sensors 125 associated with a user 120. The network 130 may comprise any combination of local area and/or wide area networks, using wired and/or wireless communication systems. In one embodiment, the network 130 uses standard communications technologies and/or protocols. For example, the network 130 can include communication links using technologies such as Ethernet, 3G, 4G, CDMA, WIFI, and Bluetooth. Data exchanged over the network 130 may be represented using any suitable format, such as hypertext markup language (HTML) or extensible markup language (XML). In some embodiments, all or some of the communication links of the network 130 may be encrypted using any suitable technique or techniques. In some implementations, the network 130 also facilitates communication between the active learning system 110, users 120, and other entities of the environment 100 such as the health system 140.

The health system 140 is a server, set of servers, server cluster, or other computing system which can create or modify an individual treatment plan and/or perform interventions based on CHC symptom predictions (such as a CHC symptom log) made by the active learning system 110. For example, the health data repository 140 can be a medical provider, doctor, or other entity providing medical care to a user 120 for a CHC. Only one health system 140 is shown in FIG. 1, however, the active learning system 110 can interface with multiple health systems 140 for different users 120.

Figure 2:
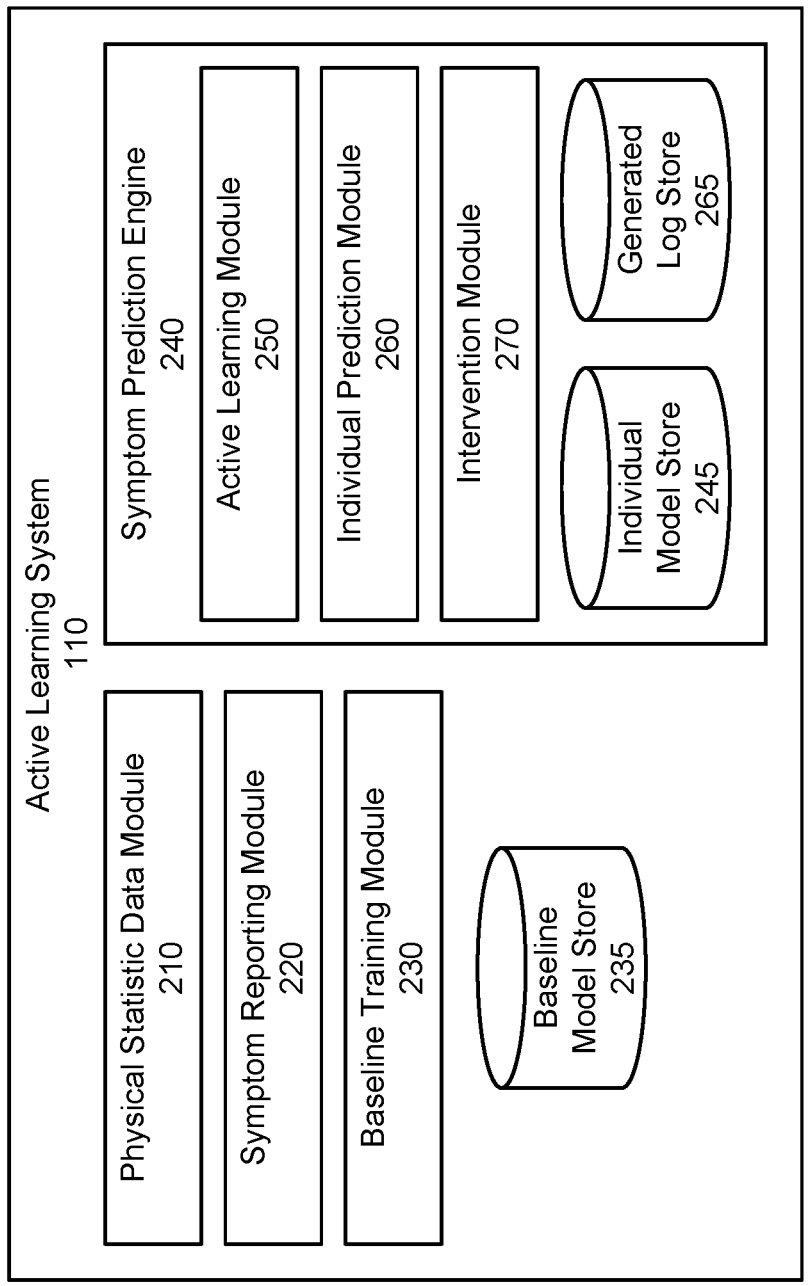
FIG. 2 is a block diagram of an active learning system, in accordance with an embodiment.

FIG. 2 is a block diagram of an active learning system, in accordance with an embodiment. FIG. 2 shows an active learning system 110 including a physical statistic data module 210, a symptom reporting module 220, a baseline training module 230 with an associated baseline model store 235, and a symptom prediction engine 240. In other embodiments, the active learning system 110 may include additional, fewer, or different components for various applications. Conventional components such as network interfaces, security functions, load balancers, failover servers, management and network operations consoles, and the like are not shown so as to not obscure the details of the system architecture. In some embodiments, active learning system 110 can monitor a set of users 120 for multiple CHCs simultaneously, as described above. In some implementations, each module of the active learning system 110 can simultaneously perform its function for multiple distinct CHCs and, in some cases, gathered data (such as physical statistic data) can be applicable to the analysis for multiple CHCs affecting the same physical statistics.

Data Gathering

The physical statistic data module 210 of the active learning system 110 can monitor a set of physical statistics about the set of users 120. In some implementations, the physical statistic data module 210 gathers time series datasets representing measures of the set of physical statistics of a user over time ("physical statistic data"). The physical statistic data module 210 can receive physical statistic data, process it for use by the active learning system 110, and store the physical statistic data. As described above, the physical statistic data for a user can include readings from one or more health sensors 125 associated with the user, however the physical statistic data module 210 can collect physical statistic data from other sources, such as by being logged or otherwise manually input by the associated user 120, from a health data repository 140, or from another similar source.

The physical statistic data module 210 can, in some embodiments, preprocess received physical statistic data prior further analysis by the active learning system 110. The active learning system 110 can receive physical statistic data from multiple different types or models of health sensors 125 (or other sources) which can report physical statistic data in different formats and using different conventions. For example, the frequency of data points in received time series data can differ between physical statistic data collected from different health sensors 125 (even if both measure the same statistics). In some implementations, the physical statistic data module 210 can standardize received physical statistic data for further analysis, such as by transforming received time series data to be consistent across the set of physical statistic data and/or computing secondary physical statistic data from received physical statistic data. For example, the physical statistic data module 210 can receive physical statistic data for a user 120 including a rolling 5 minute average of heart rate measurements and activity data for a user and preprocess the data to a daily RHR, step count, time spent active, and sleep time (for example, determined based on a combination of time, heart rate, and activity data) for the user 120 for each data was received.

Each physical statistic monitored by the active learning system 110 can be affected when a user 120 experiences symptoms of a monitored CHC. ISE, physical statistic data collected by the physical statistic data module 210 can be used both in training models (baseline and individual models) for a CHC (along with training symptom data gathered by the symptom reporting module 220) and for predicting CHC symptoms based on an individual mode models in real time or in near-real time. In some implementations, the physical statistic data module 210 continuously receives physical statistic data from health sensors 125 or users and preprocesses the physical statistic data for evaluation in real time or near-real time (for example, for predicting the current symptoms of a CHC).

The symptom reporting module 220 can receive CHC symptom reports from users 120. A CHC symptom report can identify a user 120, a relevant time period (such as the day of the CHC symptoms), and a description of the CHC symptoms or a rating of the severity of the CHC symptoms. The form and contents of CHC symptom descriptions within a CHC symptom report can depend on the CHC and the reported symptoms (for CHCs where multiple types of symptoms are monitored). For example, some CHCs may have binary symptom reporting (either the symptom was experienced on that day or not) while others may have the user 120 rate the severity of a CHC symptom on a scale (for example on a 1-5 scale). In some implementations, the symptom reporting module 220 can receive CHC symptom reports for a user 120 from another authorized source, such as a health system 140 or a third-party symptom tracking service or application (if requested by or consented to by the user 120).

Using the user 120 and time period associated with a CHC symptom report, the ALS 110 can link the CHC symptom report to physical statistic data for the user 120 as they were experiencing the CHC symptoms. The received CHC symptom reports and associated physical statistic data can be later used by the ALS 110 to train baseline CHC models for a population or to improve an individual CHC model for the reporting user 120. Users 120 can self-report CHC symptoms based on a prompt or reminder from the ALS 110 or unprompted on their own initiative. CHC symptom reports can be used to train a baseline model for a CHC or, as described above, to improve a user-specific individual model of a CHC using active learning techniques.

Baseline CHC Models

The baseline training module 230 can train CHC-specific machine learning models which can be used by the active learning system 110 to predict CHC symptoms in a user 120 based on physical statistic data for that user 120, according to some embodiments. CHC-specific machine learning models (herein, baseline CHC models) generated by the baseline training module 230 can be based on physical statistic data for multiple users 120 within a population (each of which has reported physical statistic data and made CHC symptom reports) and can be generally applicable to any user 120 within the population (and are therefore not specific to any one user 120). In some implementations, the ALS 110 uses baseline CHC models as a starting point for training individual CHC models adapted for a single user 120. Generated baseline CHC models can be stored in a database or other data storage system of the baseline model store 235 for retrieval and use by the active learning system 110.

A baseline CHC model can predict the impact of a target CHC based on physical statistic data for a defined set of physical statistics used by the baseline CHC model. In some implementations, a baseline CHC model is associated with a specific population or population cohort of users 120 selected by demographic information, geographic location, or other similar factors. The baseline training module 230 can train multiple baseline CHC models for the same CHC, with each baseline CHC model having a different combination of applicable population of users 120 and physical statistics used as inputs for prediction. For example, the baseline training module 230 can construct a baseline CHC model using a combination of RHR, step count, and sleep amount to predict the severity of chronic pain in an affected user 120. Using multiple categories of gathered physical statistic data in the same baseline CHC model can result in a more accurate baseline CHC model (and eventually individual CHC model), according to some embodiments.

A baseline CHC model can take recent physical statistic data for a user 120 (for example, containing physical statistics from the current day and 3 previous days) and return a prediction of CHC symptoms for the user 120 on the current day (herein, a CHC symptom prediction). Like CHC symptom reports, the specific form of a returned CHC symptom prediction can depend on which CHC the baseline CHC model is trained on and parameters set for the model itself. For example, a CHC model for chronic pain can be trained to make binary prediction of whether the user 120 will experience pain associated with their chronic pain (returning a yes or no for CHC symptoms). Alternatively, another CHC model for chronic pain can be trained to predict the severity of chronic pain the user 120 will experience on that day (for example, on a 5-point scale).

To train a baseline CHC model, the baseline training module 230 can assemble a training data set based on gathered physical statistic data and CHC symptom reports from the symptom reporting module 220. In some implementations, the baseline training module 230 first assembles an initial training set of users 120 associated with the target CHC. A user can be selected for the training set if the user's stored physical statistic data is associated with the target CHC (for example, placed there based on the user self-reporting having the target CHC). For example, when assembling a training data set for a target CHC the baseline training module 230 can select users 120 who are associated with the target CHC, who have made CHC symptom reports for a target CHC (or over a threshold number of CHC symptom reports), and are associated with a target set of physical statistic data that the baseline CHC model will be based on.

In some embodiments, the training data set includes all available physical statistic data for users 120 in the training data set between preset dates (for example, the months of January and February of a given year). In other implementations, analysis for each user 120 in the training data is based on physical statistic data for a time range around the known CHC symptom reports. For example, the training data set can contain data from one week before and after each CHC symptom report. The baseline training module 230 can select the length and type of timeframe for analysis based on any suitable factors, including the availability of physical statistic data and the target CHC.

In some embodiments, baseline CHC models are based on normalized physical statistic values relative to a baseline (expressed as a percentage or absolute difference from a determined baseline for the user 120 in that physical statistic). In some implementations, the baseline training module 230 can calculate per-user 120 normalized baselines of each collected physical statistic (for example, normalized RHR, step count, and a sleep amount) for each user 120 in the training data set. In other embodiments, baseline training module 230 can calculate a baseline for each physical statistic for the baseline CHC model based on physical statistic data in the days surrounding a CHC symptom report. For example, the baseline RHR for a user can include the mean and standard deviation of that user's RHR calculated for the recorded days before a CHC symptom report.

In other embodiments, the baseline training module 230 uses machine learning techniques to train baseline CHC model that take into account multiple days of context and/or more than one physical statistics to predict CHC symptoms for a user on a given day. Similarly, machine learned baseline CHC models can be trained using a combination of physical statistics as input features (such as a combination of nRHR, step count, and sleep time). The baseline training module 230 can use neural networks, deep learning techniques, gradient-boosting techniques, or another machine learning technique or combination of machine learning techniques to generate baseline CHC model based on a training data set based on user physical statistic data from the physical statistic data module 210 and CHC symptom reports collected by the illness reporting model 220. For example, the machine learning training model can use machine learning techniques such as linear support vector machine (linear SVM), boosting for other algorithms (e.g., AdaBoost), neural networks, deep learning, logistic regression, naïve Bayes, memory-based learning, random forests, bagged trees, decision trees, boosted trees, or boosted stumps in various embodiments. In some implementations, the machine learning training module can re-train baseline CHC models periodically or based on additional training data (physical statistic data and/or labeled CHC symptom reports) becoming available. As described above, baseline CHC models can be stored in the baseline model store 235 for later use by the symptom prediction engine 240. For example, the baseline training module 230 can train a machine learning model configured to predict CHC symptoms (or the severity of CHC symptoms) based on time series physical statistic data for a target user 120.

In some implementations, baseline CHC models trained by the baseline training module 230 can have a ROC AUC (the Area Under the Curve of the Receiver Operating Characteristic curve) which is too low for the baseline CHC models to serve as a reliable indicator of CHC symptoms for an individual user 120. Baseline CHC impact models can exhibit varying ROC AUC based on the machine learning techniques used and the amount, selection, and quality of physical statistic data available to be used as inputs to a baseline CHC model. An example CHC impact model (for example for chronic pain) using a combination of several physical statistics can exhibit a ROC AUC of between 0.5 and 0.6. However, as described above, the active learning system 110 does not use the baseline CHC models to directly make CHC symptom predictions, but instead as a starting point for developing individual CHC models, each specialized to predicting CHC symptoms for a specific user. After a calibration period, an example individual CHC model can exhibit a ROC AUC between 0.8 and 0.95 and can be used to reliably predict CHC symptoms.

Individual CHC Models

As described above, the active learning system 110 can use generated models to predict CHC symptoms for a user 120 based on current physical statistic data for that user 120. The symptom prediction engine 240 of FIG. 2 includes an individual model store 245, an active learning module 250, an individual prediction module 260, a generated log store 265, and an intervention module 270.

To enable the symptom prediction engine 240 to make CHC symptom predictions for an individual user 120, the symptom prediction engine 240 can deploy an individual CHC model associated with the user 120 based on an existing baseline CHC model. In some implementations, the symptom prediction engine can retrieve an appropriate baseline CHC model (for example, a baseline CHC model associated with a population the user 120 is part of and trained to predict CHC symptoms based on physical statistic data available for the user 120) to use as the initial individual CHC model for the user 120. This individual CHC model can be stored in a database or other data storage system of the individual model store 245 for use by the symptom prediction engine 240. At this stage (immediately after creation from a baseline CHC model), the individual CHC model will not be more accurate at making predictions for the user 120 than the baseline CHC model. Therefore, the symptom prediction engine 240 can use active learning techniques (such as Bayesian sequential active learning) to adapt the initial individual CHC model its associated user 120 and improve the accuracy of the individual CHC model in predicting CHC symptoms for the user 120. As a certain minority of users 120 in a given population can exhibit opposite to trend behavior in one or more physical statistics (for example, a minority of users of a certain CHC may experience a drop in RHR when experiencing severe symptoms as opposed to an increase in nRHR as can be expected based on an average user) and individual CHC model can be more accurate in making CHC symptom predictions than a baseline model trained over a population.

The individual model store 245 can include a data storage system such as a database or file storage system based on a server, server cluster, or other computing device of the active learning system 110. Individual CHC models stored by the individual model store 245 can include the individual CHC model itself, an indication of the associated user 120, and associated user-specific training data (such as CHC symptom reports) from the associated user.

The active learning module 250 can improve and maintain individual CHC models using active learning machine learning techniques. For example, the active learning module 250 can use a version of Bayesian Sequential Active Learning, active learning techniques using Support Vector Machines, Bayesian Active Learning by Disagreement (BALD), and/or other active learning techniques. The active learning module 250 can monitor the performance of individual CHC models (for example, via an uncertainty value for a given prediction of the model) and decide to make a prediction using the individual CHC model and/or request feedback from the associated user 120 to improve the individual CHC model.

In some embodiments, the active learning module 250 generates an uncertainty value for each potential CHC symptom prediction, where the uncertainty value for a prediction approximately reflects a probability that the CHC symptom prediction will be correct. An uncertainty value can be generated for a potential prediction (prior to the prediction being made), concurrently with the associated prediction, or based on an existing prediction. Uncertainty values for CHC symptom predictions can be calculated using Maxent, mutual information between the CHC symptom predictions and individual CHC model posterior, variation ratio, or another measure of uncertainty. Depending on the specific active learning technique used, an uncertainty value for a CHC symptom prediction can be an estimated probability of correctness (or incorrectness) or may be a relative value used to compare uncertainty between CHC symptom predictions for different days (or other time period between predictions). In some implementations, uncertainty values are analyzed to minimize an uncertainty budget over a series of predictions (for example, trying to minimize total uncertainty over a set of time periods). Uncertainty values can be used by the active learning system 250 to determine whether to rely on a CHC symptom prediction or to request confirmation or feedback from a user to supplement or replace the CHC symptom prediction.

Before making any predictions with a newly deployed individual CHC model, the active learning module can perform a calibration or "run in" period to adapt the individual CHC model to the specific characteristics of the associated user 120 (not only to the broad trends captured by the baseline CHC model). In some implementations, during the calibration period the active learning module 250 regularly requests CHC symptom reports from the associated user 120. For example, the active learning module 250 can send a message or other notification to a client device or email of a user 120 requesting the user 120 to provide a CHC symptom report for the day (for example, via the symptom reporting module 220). Using the additional (associated user-specific) data from the calibration period, the active learning module 250 updates the individual CHC model using the received CHC symptom reports and the linked physical statistic data gathered from the associated user 120. As described above, an individual CHC model can more closely reflect the specific situation of the user 120 such that the individual CHC model can be used to make more accurate CHC symptom predictions for the user 120 when compared to a baseline CHC model not adapted to any specific user 120. Updates to an individual CHC model during the calibration period can occur continuously as new CHC symptom data is received or at the end of the calibration period.

A calibration period can be a predetermined length (for example, 10 days) or can last until a target amount of user-specific CHC symptom reports are received from the associated user 120, even if the received CHC symptom reports are non-consecutive or some days are skipped (for example, lasting until the user 120 has provided 10 CHC symptom reports). In other implementations, a calibration period can have a variable duration based on an estimated deviation of the associated user 120 from an average user or based on existing CHC symptom reports from the associated user 120 available to the symptom prediction engine 240. For example, a user 120 may have already provided initial CHC symptom reports and physical statistic data used to train a baseline CHC model, or may have manually logged CHC symptom reports with the active learning system 110 (or with another source authorized to send the CHC symptom reports to the user) before opting in to the symptom prediction engine 240 that can be linked to historical physical statistic data for the associated user 120.

After the calibration period, the individual CHC model is ready for use in making CHC symptom predictions for the associated users. The active learning module 250 can use one or more active learning techniques to improve or maintain the individual CHC model's accuracy concurrently with making CHC symptom predictions. In some implementations, the active learning module 250 receives physical statistic data for the associated user 120 and calculates an uncertainty value for a potential CHC symptom prediction using for the received physical statistic data using the individual CHC model. Using the uncertainty value, the active learning module 250 can determine whether to make an active learning request and/or cast a CHC symptom prediction using the individual CHC model as is. After receiving a response to an active learning request from the user 120 can update and/or retrain the individual CHC model with the additional training data from the response to the active learning request. Active learning can enable individual CHC models to be gradually revised to take into account situations not reflected in the baseline CHC model or previous user 120 specific training data.

To make an active learning request, the active learning module 250 sends a message or other communication to the associated user 120 (for example, via a mobile device of the user 120) requesting additional data (such as a CHC symptom report) to improve the training data of their individual CHC model. The active learning module 250, according to some embodiments, can send multiple type of active learning requests requiring different levels of effort and interaction from the user 120. For example, a full active learning request can request a CHC symptom report from the user 120 without providing any prediction or suggestions that might influence the user's response. In contrast, a confirmation-style active learning request can provide a current CHC symptom prediction from the individual CHC model and request that the user actively approve or reject the prediction. In other implementations, additional or different styles of active learning requests can be implemented by the active learning module 250 (such as an informative active learning request which informs the user 120 of a CHC symptom prediction and reminds them to manually correct the prediction if it is wrong). In some implementations, the maximum rate at which an active learning module 250 can request CHC symptom reports (the "request rate") is limited to reduce interruptions and inconvenience to the associated user 120. The request rate can be limited using any suitable rule, for example, to a request rate of $r=\frac{1}{3}$ (1 request every 3 days), $\frac{2}{7}$ (2 requests per week, which may be on consecutive days), or the like. Each type of active learning request can be weighed differently within the request rate or may have separate request rates (for example, with more inconvenient active learning requests being weighted more heavily or having a lower request rate). On each day, the active learning module 250 can use an acquisition function to determine whether to request a CHC symptom report from the associated user 120 based on an uncertainty value calculated for the current day, the request rate, and previously made requests (to prevent exceeding the request rate).

For example, in some embodiments the active learning system 110 uses a simple acquisition function which compares an uncertainty value for the current day to an uncertainty threshold to determine whether to make a prediction or request a CHC symptom report for the current day (where an uncertainty above the threshold would lead to requesting additional data from the user 120). Uncertainty thresholds can be static, user-specific, or calculated dynamically (for example, based on the number of recent CHC symptom requests to the user 120 or if the active learning module 250 is close to exceeding the request rate). In some implementations, the active learning module 250 uses separate uncertainty thresholds for each type of active learning request used by the active learning module 250. For example, the uncertainty threshold for making a full active learning request can require a higher uncertainty than making a confirmation active learning request. A dynamically calculated uncertainty threshold can, for example, be based on an estimated probability distribution of uncertainty values for the individual CHC model, where the uncertainty threshold is set such that a CHC prediction is requested when the current uncertainty $x>\text{quantile}(D, 1-r)$ where D is the distribution of uncertainty values and r is the request rate. This method of calculating a dynamic threshold results in the top r of uncertainty values triggering an active learning request (for example, if $r=\frac{1}{3}$, the top third of uncertainty values would result in an active learning request). As more predictions are made by the individual CHC model, the distribution D of likely uncertainty values can shift (and the dynamic uncertainty threshold can shift with it. Using a dynamic uncertainty threshold can prompt the active learning module 250 to respond to dataset shifts that over time impair model performance and safety.

In other embodiments, the active learning module 250 can use an advanced acquisition function that takes into account, for example, the potential of making requests in the future to determine whether to make an active learning request. For example, the active learning module 250 can use a "token bucket" style algorithm to constrain active learning requests to the request rate while also asymptotically selecting the days with the top uncertainty values for active learning requests. An example token bucket implementation adds a token to a "token bucket" every 1/r days, where the bucket can hold at the most b tokens (tokens arriving when the bucket is full are discarded). If no tokens are available, the active learning module casts a CHC symptom prediction for the current day using current physical statistic data. If one or more tokens are available, the active learning module 250 can perform additional analysis to determine if an active learning request should be made. In some implementations, the active learning module can calculate an uncertainty value for the current day and a dynamic uncertainty threshold for making an active learning request and use the dynamic threshold to determine whether to make an active learning request or not. For example, the active learning module 250 can use the estimated probability distribution method (described above) for determining the dynamic threshold. If an active learning request is made a token is consumed from the token bucket, whereas tokens are allowed to accumulate if a CHC symptom prediction is made (leaving them available for making future active learning requests).

The individual prediction module 260 can, according to some embodiments, cast and store CHC symptom predictions from individual CHC models. In some embodiments, the individual prediction module 260, receives current CHC symptom predictions from the active learning module 250 (for example, predictions calculated while deciding whether to make an active learning request). In other embodiments, the active learning module 250 instructs the individual prediction model to cast a prediction for the current day. In response to an instruction to cast a prediction, the individual prediction module 260 can retrieve the current physical statistic data from the associated user 120 (or the relevant data can be provided by the active learning module 260) and input the gathered physical statistic data into the individual CHC model. The resulting CHC symptom prediction can then be stored in a log for tracking and later reference by the active learning system 110, the user 120, or a health system 140. The log of CHC symptom predictions for an individual CHC model can be stored in a database or other data storage system of the generated log store 265 for later reference by the symptom prediction engine 240.

The generated log store 265 can include a data storage system such as a database or file storage system based on a server, server cluster, or other computing device of the active learning system 110. CHC symptom predictions from an individual CHC model can be stored in a log, table, or database of the generated log store 265 for that individual CHC model. A log for an individual CHC model can include the set of CHC predictions, CHC symptom reports (covering instances where the user has responded to an active learning request or manually updated the log), an indication of the associated user 120, and, in some embodiments, a record of uncertainty values for the CHC predictions in the log.

The intervention module 270 can recommend or automatically perform interventions based on CHC predictions made by the individual prediction module 260. Interventions recommended by the intervention module 270 can notify the user of the potential CHC, mitigate the impact of the CHC on a population, treat the CHC symptoms (in some cases automatically), alert a healthcare provider, or provide for further diagnosis of the CHC, according to some embodiments. The interventions taken by the intervention module 270 can depend on the CHC, the user 120 (for example, based on user demographics, available information about the user 120, and/or preference settings of the user. In some implementations, the intervention module 270 can allow the associated user 120 or an authorized health system 140 to review the log of CHC symptom predictions for the associated user 120. Similarly, the intervention module 270 can provide an interface for the associated user 120 to manually correct or otherwise update previous CHC symptom predictions.

In some embodiments, the intervention module 270 can determine if an intervention is appropriate each time a CHC symptom prediction is cast by the individual prediction module. Each CHC monitored by the active learning system 110 can be associated with a set of one or more possible interventions that can be initiated by the intervention module 270 based on CHC symptom predictions for the CHC. A single CHC symptom prediction can result in more than one intervention for the associated user 120 and a single intervention can be based on more than one CHC symptom predictions made over a period of time. In some implementations, each intervention is associated with an intervention threshold and/or other intervention criteria which the intervention module 270 uses to determine if the intervention should be initiated for a given user 120. In addition, the intervention module 270 can select to initiate (or not initiate) an intervention based on additional factors (in combination with the CHC prediction), such as user 120 demographics or preference selections, or other selected interventions (for example, interventions may be mutually exclusive or counterproductive if performed together).

In some implementations, the set of interventions associated with a CHC can include one or more messages sent to the user 120 notifying the user of the CHC symptom prediction and including instructions to mitigate the effects of the CHC on that day. For example, the intervention module 270 can send a message to a user 120 notifying the user of a CHC symptom prediction of higher than average symptom severity and instruct the user to take preventative steps (depending on the CHC). For example, a user could refrain from strenuous physical activities or avoid actions that might trigger CHC symptoms. If the CHC is a migraine headache such a message might read "you have a high chance of getting a migraine today, consider avoiding your migraine triggers." Similarly, the intervention module 270 can use pattern recognition techniques to try to try to identify triggers for CHC symptoms. The set of interventions associated with a CHC can also include sending an alert to a healthcare professional (for example, via the health system 140) without explicit input from the user 120 and/or the automatic administration of a medicine or compound via a user-worn delivery device (for example, the device containing the health sensor 125).

In some implementations, the intervention module 270 can perform interventions which configure the health sensor 125 gathering data from the user 120. For example, the intervention module 270 can increase the rate at which data is gathered and/or reported by the health sensor 125, change a type of data collected by the health sensor 125, or cause the health sensor 125 to beep, display an alert to the user 120 (either immediately or on a schedule), play an alarm to wake the user 120 or a partner of the user 120 up, or display a notification to the user 120.

Example Active Learning

Figure 3:
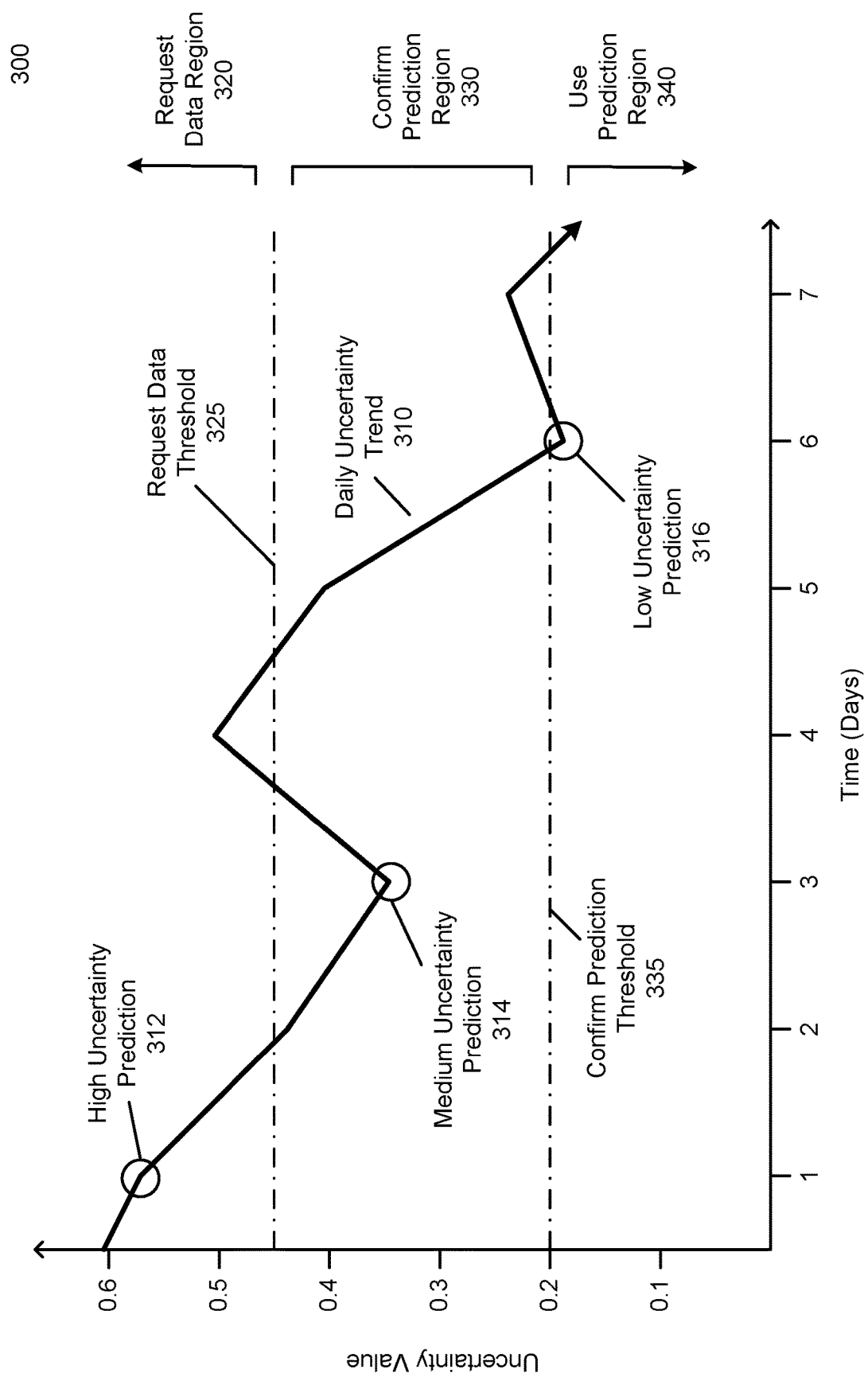
FIG. 3 is a graph illustrating an example uncertainty trend for a chronic health condition model, according to one embodiment.

FIG. 3 is a graph illustrating an example uncertainty trend for a chronic health condition model, according to one embodiment. The graph 300 of FIG. 3 shows a daily uncertainty trend 310 graphing the uncertainty value associated with CHC symptom predictions over a time (measured in days in the embodiment of FIG. 3). FIG. 3 highlights a high uncertainty prediction 312, medium uncertainty prediction 314, and low uncertainty prediction 316 out of the set of predictions making up the daily uncertainty trend 310. The embodiment of FIG. 3 uses uncertainty thresholds (the request data threshold 325 and the confirm prediction threshold 335) to control the sending of active learning requests. The uncertainty thresholds divide the graph 300 into a request data region 320, a confirm prediction region 330, and a use prediction region 340.

On the first day shown by the graph, the active learning module 250 calculates a high uncertainty value for a prediction made with the available physical statistic data (represented by the high uncertainty prediction 312). This uncertainty value of the high uncertainty prediction 312 is above the request data threshold 325 (and in the request data region 320), accordingly, the active learning module can elect to make an active learning request to the user seeking a CHC symptom report. Using the results of the active learning request, the active learning module 250 can retrain the individual CHC model and hopefully reduce future uncertainty values. As described above, depending on the request rate, an active learning request may not be an option.

A few days later the medium uncertainty prediction 314 is made by the symptom prediction engine 240. Comparatively, the uncertainty value associated with the medium uncertainty prediction 314 is lower than the high uncertainty prediction 312 and is below the request data threshold 325. Consequently, the active learning module 250 can make a prediction but, as the uncertainty value of the medium uncertainty prediction 314 is still above the confirm prediction threshold 335 (and in the confirm prediction region 330), send an active learning request including the medium uncertainty prediction 314 and instructing the associated user 120 to confirm or correct the provided prediction.

The low uncertainty prediction 316 is generated after several mode days, as this prediction has an uncertainty value below any uncertainty threshold (i.e. the low uncertainty prediction 316 is in the use prediction region 340), the active learning module elects not to make any active learning requests based on the low uncertainty prediction 316 and enter the low uncertainty prediction 316 into a log of CHC symptom predictions for the associated user 120 without making an active learning request.

Active Learning System Processes

Figure 4:
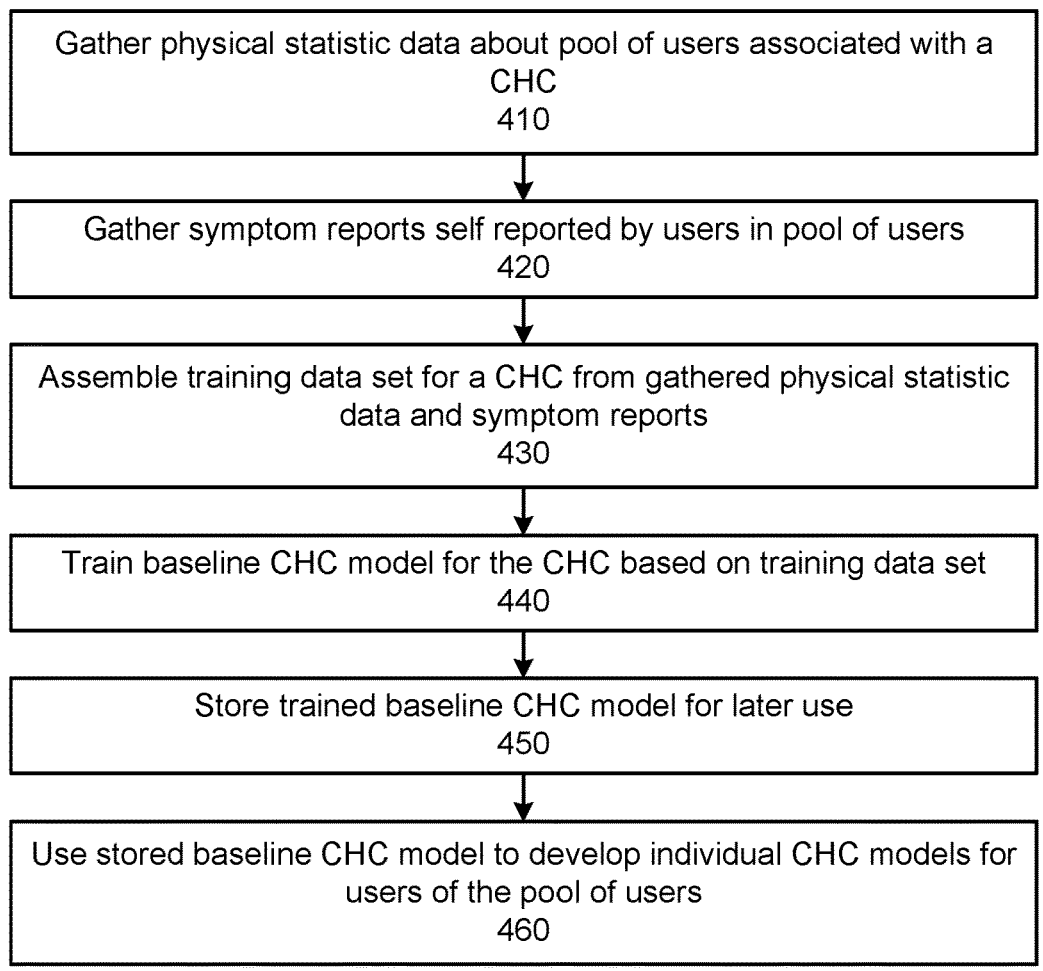
FIG. 4 is a flowchart illustrating an example process for training a baseline model of a chronic health condition at an active learning system, according to an embodiment.

FIG. 4 is a flowchart illustrating an example process for generating a baseline model of a chronic health condition at an active learning system, according to an embodiment. The process 400 of FIG. 4 begins when an active learning system gathers 410 physical statistic data about a pool of users with a CHC. For example, as described above, the active learning system can gather information from one or more health sensors of users of the active learning system. Then, the active learning system can gather 420 CHC symptom reports describing symptoms of the CHC among the pool of users. For example, self-reported accounts of daily symptoms. Next, the active learning system assembles 430 a training data set for the CHC using the gathered physical statistic data and CHC symptom reports and trains 440 a baseline CHC model for the CHC based on the assembled training data set. The trained baseline CHC model can then be stored 450 and used 460 to develop individual CHC models for individual users.

Figure 5:
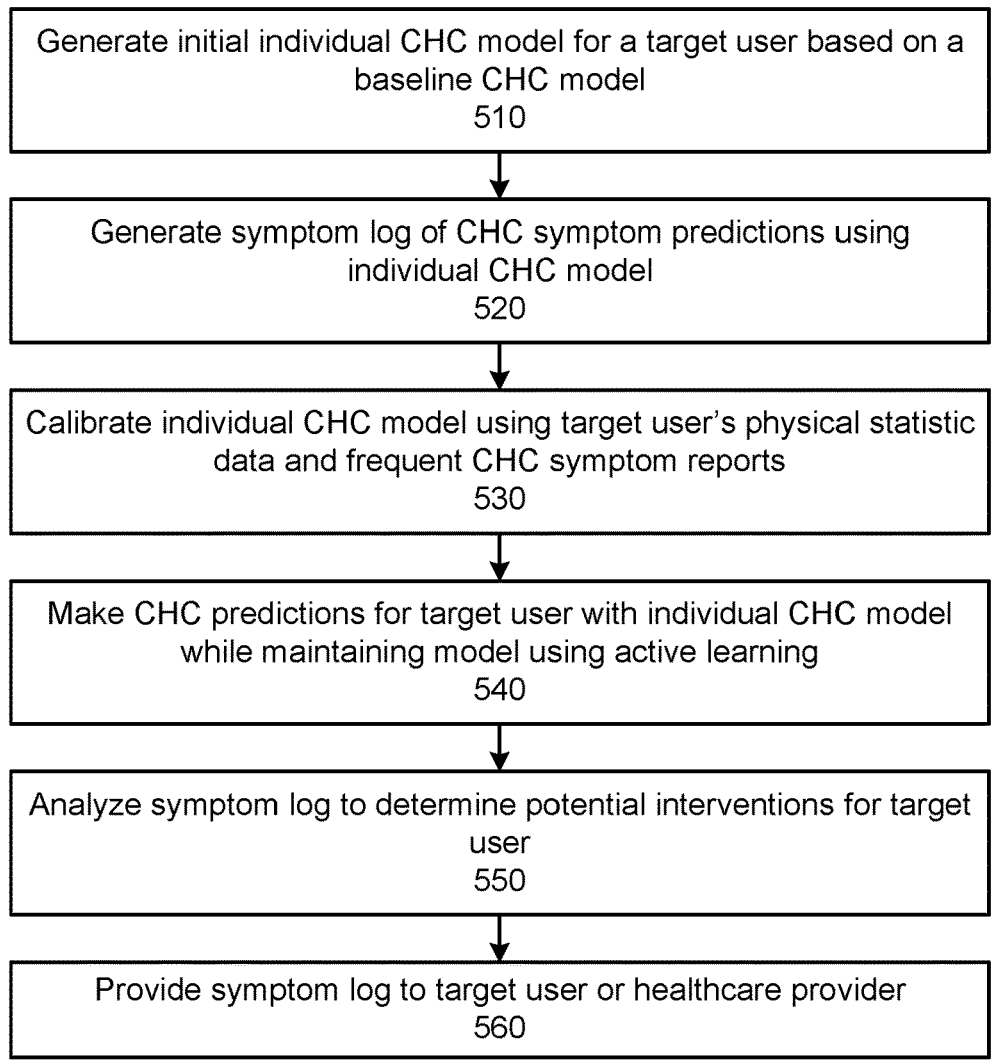
FIG. 5 is a flowchart illustrating an example process for applying an individualized model of a chronic health condition to predict symptoms in a target user, according to an embodiment.

FIG. 5 is a flowchart illustrating an example process for using an individualized model of a chronic health condition to predict symptoms in a target user, according to an embodiment. The process 500 of FIG. 5 begins when the active learning system generates 510 an initial individual CHC model for a target user based on an existing baseline CHC model and 520 a symptom log to hold CHC symptom predictions using individual CHC model. The active learning system then places the individual CHC model in a calibration period where the active learning system calibrates 530 the individual CHC model using the target user's physical statistic data and frequent CHC symptom reports to adapt the individual CHC model to the target user. After the calibration period, the active learning module makes 540 CHC predictions for storage in the symptom log using the individual CHC model while maintaining the model using active learning techniques. The active learning system can also analyze 550 symptom log to select and send interventions to the target user and provide 560 the symptom log to the target user or an authorized healthcare provider.

Figure 6:
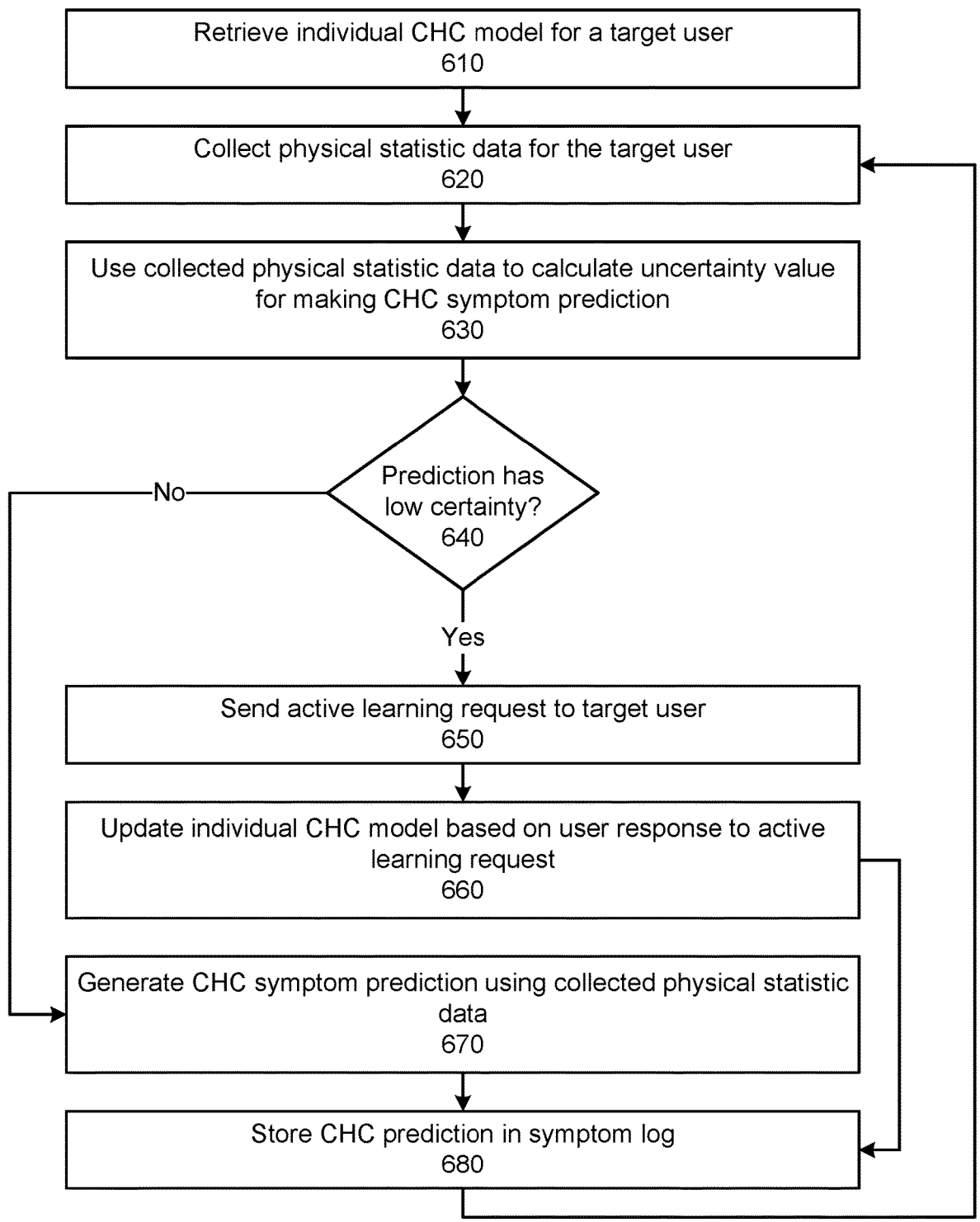
FIG. 6 is a flowchart illustrating an example process for maintaining an individualized model of a chronic health condition at an active learning system, according to an embodiment.

FIG. 6 is a flowchart illustrating an example process for maintaining an individualized model of a chronic health condition at an active learning system, according to an embodiment. The process 600 of FIG. 6 begins when an active learning system retrieves 610 an individual CHC model for a target user and collects 620 the target user's physical statistic data to make a prediction. Using the collected physical statistic data, the active learning system calculates 630 an uncertainty value for a CHC symptom prediction based on the collected data. If a prediction made using the collected data has a low certainty 640 (for example, if the uncertainty is above a threshold value), the active learning system sends 650 an active learning request to the target user to get additional information corresponding to the collected physical statistic data to improve the individual CHC model for the target user. The active learning system can then update 660 the individual CHC model based on the target user's eventual response to the active learning request. In some implementations, the user's response to the active learning request is stored 680 in the symptom log in place of a CHC prediction. Alternatively, if no active learning request for additional data is required 640 (for example, if the uncertainty value is below the threshold for requesting input from the target user), the active learning system generates 670 CHC symptom prediction based on the collected physical statistic data. The CHC prediction is then stored 680 in a symptom log for the target user and the process can repeat from step 620 the next time a CHC symptom prediction is needed.

CONCLUSION

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Some portions of this description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights, which is set forth in the following claims.

What is claimed is:

1. A method comprising:
   accessing a set of training data for a plurality of users of a population, the training data representative of physical statistics and symptoms for the plurality of users for each of a plurality of time periods;
   training a baseline machine learning model using the accessed set of training data, the baseline machine learning model configured to predict, at a frequency equal to or less than once a day, for a first chronic health condition, chronic health condition symptoms for a user based on physical statistics of the user;
   accessing, for a target user, a set of target training data representative of physical statistics and symptoms of the target user for one or more time periods;
   training an individual machine learning model using the accessed set of target training data and the baseline machine learning model, the individual machine learning model configured to predict, at a frequency equal to or less than once a day, for the first chronic health condition, chronic health condition symptoms for the target user based on subsequently-received physical statistics of the target user;
   calculating an uncertainty value for a prediction from the individual machine learning model; and
   in response to the uncertainty value for the prediction being greater than a threshold value, determining if a request rate is exceeded if additional information is requested from the target user, wherein the threshold value comprises a dynamically calculated threshold based on a distribution of previous uncertainty values and the request rate.

2. The method of claim 1, wherein the first chronic health condition comprises one or more of: chronic pain, migraine headaches, multiple sclerosis, chronic obstructive pulmonary disease, a physical injury, or a treatment regimen with side effects.

3. The method of claim 1, further comprising, in response to the uncertainty value for the prediction being greater than a threshold value and determining that the request rate is not exceeded if the additional information is requested from the target user:
   requesting, from the target user, the additional information, wherein the additional information is representative of the physical statistics and the symptoms of the target user;
   receiving, from the target user, the additional information; and
   retraining the individual machine learning model based on the additional information, thereby generating an updated individual machine learning model.

4. The method of claim 3, further comprising:
   in response to an updated uncertainty value for a prediction of the updated individual machine learning model being less than the threshold value:
   generating, based on the updated individual machine learning model and the physical statistics data for the target user, an updated symptom prediction for the target user; and
   adding the updated symptom prediction to a symptom log of the target user.

5. The method of claim 1, wherein the physical statistics of the set of target training data comprises one or more measurements of a physical statistic selected from the group consisting of resting heart rate, activity level, daily step count, and sleep time.

6. The method of claim 1, wherein the physical statistics of the set of target training data comprises step count.

7. The method of claim 1, wherein the set of target training data comprises time series measurements of at least one of the physical statistics from a wearable health sensor of at least one of the plurality of users.

8. One or more non-transitory computer-readable media comprising computer-executable instructions that, when executed by at least one processor, cause the at least one processor to:
   access a set of training data for a plurality of users of a population, the training data representative of physical statistics and symptoms for the plurality of users for each of a plurality of time periods;
   train a baseline machine learning model using the accessed set of training data, the baseline machine learning model configured to predict, at a frequency equal to or less than once a day, for a first chronic health condition, chronic health condition symptoms for a target user based on physical statistics of the target user;
   access, for a target user, a set of target training data representative of physical statistics and symptoms of the target user for one or more time periods;
   train an individual machine learning model using the accessed set of target training data and the baseline machine learning model, the individual machine learning model configured to predict, at a frequency equal to or less than once a day, for the first chronic health condition, chronic health condition symptoms for the target user based on subsequently-received physical statistics of the target user;
   calculate an uncertainty value for a prediction from the individual machine learning model; and
   in response to the uncertainty value being greater than a threshold value, determine if a request rate is exceeded if additional information is requested from the target user, wherein the threshold value comprises a dynamically calculated threshold based on a distribution of previous uncertainty values and the request rate.

9. The one or more non-transitory computer-readable media of claim 8, wherein the computer-executable instructions, when executed by the at least one processor, further cause the at least one processor to:
   in response to the uncertainty value for the prediction being greater than the threshold value and determining that the request rate is not exceeded if the additional information is requested from the target user:
   request, from the target user, the additional information, wherein the additional information is associated with the physical statistics and the symptoms of the target user;
   receive, from the target user, the additional information; and
   retrain the individual machine learning model based on the additional information, thereby generating an updated individual machine learning model.

10. The one or more non-transitory computer-readable media of claim 9, wherein requesting, from the target user, the additional information comprises sending a communication to the target user, the communication comprising a prediction from the individual machine learning model and a request to confirm the prediction.

11. The one or more non-transitory computer-readable media of claim 8, wherein determining if the uncertainty is greater than the threshold value further comprises using a token bucket algorithm to determine if the request rate is exceeded.

12. The one or more non-transitory computer-readable media of claim 8, wherein accessing the physical statistics for the target user comprises receiving time series measurements from a wearable health sensor of the target user.

13. The one or more non-transitory computer-readable media of claim 8, wherein the set of training data further comprises chronic health condition symptom data for the plurality of users.

14. The one or more non-transitory computer-readable media of claim 8, wherein the physical statistics comprise a measurement selected from the group consisting of resting heart rate, activity level, daily step count, and sleep time.

15. The one or more non-transitory computer-readable media of claim 8, wherein the physical statistics a measurement selected from the group consisting of respiration rate, heart rate variability, and galvanic skin response.

16. A system comprising:
   a processor; and
   a non-transitory computer-readable storage medium comprising instructions which, when executed by the processor, cause the processor to perform the operations of:
      accessing a set of training data for a plurality of users of a population, the training data representative of physical statistics and symptoms for the plurality of users for each of a plurality of time periods;
      training a baseline machine learning model using the accessed set of training data, the baseline machine learning model configured to predict, at a frequency equal to or less than once a day, for a first chronic health condition, chronic health condition symptoms for a user based on physical statistics of the user;
      accessing, for a target user, a set of target training data representative of physical statistics and symptoms of the target user for one or more time periods;
      training an individual machine learning model using the accessed set of target training data and the baseline machine learning model, the individual machine learning model configured to predict, at a frequency equal to or less than once a day, for the first chronic health condition, chronic health condition symptoms for the target user based on subsequently-received physical statistics of the target user;
      calculating an uncertainty value for a prediction from the individual machine learning model; and
      in response to the uncertainty value for the prediction being greater than a threshold value, determining if a request rate is exceeded if additional information is requested from the target user, wherein the threshold value comprises a dynamically calculated threshold based on a distribution of previous uncertainty values and the request rate.

17. The system of claim 16, wherein the operations further comprise:
   in response to the uncertainty value for the prediction being greater than the threshold value and determining that the request rate is not exceeded if the additional information is requested from the target user:
   request, from the target user, the additional information, wherein the additional information is associated with the physical statistics for the target user;
   receive, from the target user, the additional information; and
   retrain the individual machine learning model based on the additional information, thereby generating an updated individual machine learning model.

18. The system of claim 17, wherein the physical statistics for the target user comprises a measurement selected from the group consisting of resting heart rate, activity level, daily step count, and sleep time.

19. The system of claim 17, wherein receiving physical statistics for the target user comprises receiving time series measurements of at least one of the physical statistics from a wearable health sensor of the target user.

* * * * *